United States Patent
Clar et al.

(10) Patent No.: US 7,610,802 B2
(45) Date of Patent: Nov. 3, 2009

(54) DEVICE FOR MEASURING AND MONITORING THE FRACTIONAL LOAD OF ORTHOPEDIC AND SURGICAL PATIENTS

(76) Inventors: Heimo Clar, St. Peterhauptstrasse 31 F, Graz (AT) A-8042; Egon Winter, Hans Brandstattergasse 7, Graz (AT) A-8020

( * ) Notice: Subject to any disclaimer, the term of this patent is extended or adjusted under 35 U.S.C. 154(b) by 736 days.

(21) Appl. No.: 10/559,250

(22) PCT Filed: Jun. 18, 2003

(86) PCT No.: PCT/AT03/00173

§ 371 (c)(1),
(2), (4) Date: Apr. 25, 2006

(87) PCT Pub. No.: WO04/000195

PCT Pub. Date: Dec. 31, 2003

(65) Prior Publication Data

US 2006/0273913 A1  Dec. 7, 2006

(30) Foreign Application Priority Data

Jun. 19, 2002 (AT) ............................... A 925/2002
Dec. 16, 2002 (AT) ............................. A 1870/2002

(51) Int. Cl.
*A61B 5/00* (2006.01)
(52) U.S. Cl. ................... 73/172; 600/592; 340/573.1
(58) Field of Classification Search .............. 73/172; 600/592; 340/573.1
See application file for complete search history.

(56) References Cited

U.S. PATENT DOCUMENTS

| | | | |
|---|---|---|---|
| 3,702,999 A * | 11/1972 | Gradisar | 340/573.1 |
| 3,791,375 A * | 2/1974 | Pfeiffer | 600/592 |
| 4,647,918 A * | 3/1987 | Goforth | 340/573.1 |
| 5,042,504 A * | 8/1991 | Huberti | 600/592 |
| 5,285,022 A * | 2/1994 | Antone | 177/253 |
| 5,323,650 A * | 6/1994 | Fullen et al. | 73/172 |
| 5,357,696 A * | 10/1994 | Gray et al. | 36/136 |
| 5,408,873 A * | 4/1995 | Schmidt et al. | 73/862.625 |
| 5,492,066 A * | 2/1996 | Nozaki et al. | 104/93 |
| 5,511,571 A | 4/1996 | Adrezin et al. | 135/66 |
| 5,608,599 A * | 3/1997 | Goldman | 361/283.1 |
| 5,619,186 A * | 4/1997 | Schmidt et al. | 340/573.1 |
| 5,840,047 A * | 11/1998 | Stedham | 600/587 |
| 6,174,294 B1 * | 1/2001 | Crabb et al. | 600/592 |
| 6,273,863 B1 | 8/2001 | Avni et al. | 600/587 |

FOREIGN PATENT DOCUMENTS

EP  1 040 811  3/2000
FR  2 638 340  10/1988

* cited by examiner

*Primary Examiner*—Andre J Allen
(74) *Attorney, Agent, or Firm*—Thomas R. Vigil

(57) ABSTRACT

The invention relates to a device for measuring and motoring the fractional load of orthopaedic and surgical patients, comprising at least one measuring device for the direct and indirect determination of the weight load of a lower extremity, and additionally at least one alarm transmitter (17) which emits an alarm signal when an adjustable load exceeds or falls below a threshold.

9 Claims, 3 Drawing Sheets

Figure 1:
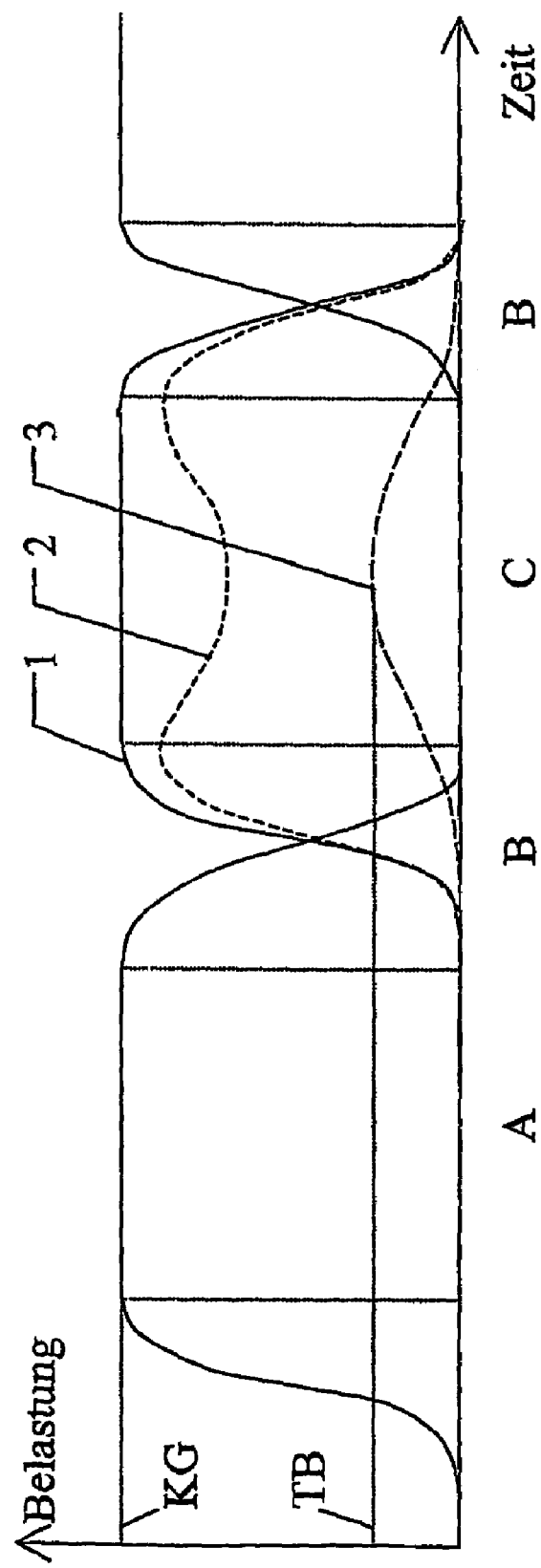

DEVICE FOR MEASURING AND MONITORING THE FRACTIONAL LOAD OF ORTHOPEDIC AND SURGICAL PATIENTS

The invention relates to a system for measuring and monitoring the partial weight load borne by orthopedic and surgical patients.

In emergency and orthopedic surgery, physicians practicing conservative therapy and, in some cases, surgical therapy are confronted with the fact that the patient must not place full weight on the injured extremity if a definite curative effect showing satisfactory results is to be achieved. If a lower extremity is affected, the patient may place only partial weight thereon with the aid of crutches.

Bearing a partial weight load is important, however, since only when pressure is applied to the bone involved is a stimulus aroused for sufficient bone growth. Thus if partial weight is not borne as soon as possible, it is doubtful whether the osseous therapy will achieve good results. And modern early functional treatment demands that a patient be mobilized as early as possible.

Partial weight bearing calls for a great deal of cooperation and circumspection on the part of the patient, who must follow precise therapeutical schemes and place a weight load on the leg involved which will vary according to diagnosis and therapy. For example, he may be required to apply a weight load of 10 kg to his leg for a period of 3 weeks. This clearly gives rise to problems due to the absence of an exact sensory apparatus for weight in the sole of the human foot.

Presently the patient is trained by means of scales to learn how much weight he must place on the scales in order to achieve the exact weight loading required. Thus modern medicine striving for therapeutic precision is confronted here by an inexact and fault-prone solution often producing poor results which might end in reoperation.

By reason of the fact that such high demands of cooperation and diligence are placed on patients of all age-groups showing various degrees of compliance, the solution presented hitherto, which was not devised for such a diversity of patients, has now become obsolete.

The following systems are known:

American Patent Specification U.S. Pat. No. 5,357,696 A (FAERE, JOHN) (Oct. 25, 1994) shows a device for measuring the force (weight force) exerted on the foot of the patient when standing or walking. An integrated alarm is provided which informs the patient that a predefined threshold has been exceeded. This alarm comprises a vibration generator.

A recording and analyzing unit (evaluation unit) is also provided.

Transmission of the measured values can be effected using electric wiring or by radio transmission.

The entire system is devised to be installed in a shoe.

Since the threshold is programmable, it is possible to set several, i.e. an arbitrary number of, upper limits.

French Laid-open Specification FR 2 638 340 (UNIVERSITÉ CLERMONT FERRANT) (4 May 1990) shows a sensor for crutches or prostheses and orthopedic devices that is adapted to measure the weight (the downwardly exerted force) bearing thereon. The signal that is produced is amplified and stored in memory. An alarm signal generator is provided which produces acoustic, tactile or optical signals as a warning.

Both an upper and a lower load bearing limit can be predefined. These alarm devices are built into the handle.

European Laid-open Specification EP 1 040 811 A2 (MOLNAR) (4 Oct. 2000) shows a crutch as defined in the present application in which measurement is carried out by means of a pressure cylinder.

These methods suffer from the following disadvantages:

According to American Patent Specification U.S. Pat. No. 5,357,696 A, the measuring device is built into a shoe. This is cost-intensive for technical reasons (involves orthopedic cobbling) and is also not hygienic in the case of a partial weight bearing time lasting several months. This method is expensive on account of the fact that the measuring device cannot be reused.

French Laid-open Specification FR 2 638 340 A and the European pendant thereof EP 1 040 811 A2 exhibit no synchronization of the measuring parameters of the two crutches or measure only the weight load on one crutch, which leads to inaccurate measured values.

It is an object of the invention to provide a system which produces sufficiently accurate measured values and by means of which good therapeutic results can be achieved in a manner presenting no complications to the patient.

This object is achieved by means of a system as defined above which, according to the invention, consists of at least one measuring device for direct or indirect determination of the weight load on a lower extremity and also of at least one alarm signal generator which produces an alarm signal when an adjustable upper limit of said weight load is exceeded.

The emission of an alarm signal warns the patient that he is placing more weight on the extremity involved than is favorable for the therapy used, so that he will experience no difficulty in avoiding such weight loading. The upper limit can be varied for different patients depending on the desired or necessary loading so that the system of the invention can be simply adapted for various patients.

It may be advantageous for at least one measuring device to be coupled to an evaluation system.

In a first embodiment of the invention, the at least one measuring device and the at least one alarm signal generator (giving, say, an acoustic alarm or a vibration alarm) and optionally the evaluation circuit are built into one or more crutches. This embodiment is simple to realize and offers cost advantages, since the crutches can be passed on to another patient when therapy is done.

In other embodiments, the measuring device is built into the sole of a shoe, an insole, or the "walking heel" of a walking cast. This is suitable, for example, for persons for whom the use of crutches is not necessary or who must in any case wear a plaster cast.

The patient will be easily warned if the at least one alarm signal generator is adapted so as to give an acoustic alarm when an adjustable upper weight bearing limit is exceeded.

A less noticeable solution is provided when the at least one alarm signal generator is adapted so as to give a vibration alarm when the partial weight load falls short of or exceeds an adjustable limit.

In order that a therapist or doctor can subsequently discern the weight loadings, an advantageous embodiment provides that when partial weight bearing exceeds the adjustable upper limit or falls short of a lower limit the value of the weight loading is recorded and stored in an electronic non-volatile memory.

Finally, it may also be advantageous to provide a number of adjustable upper limits and lower limits and to adapt the system such that for values above or below the different weight bearing limits different alarm signals, for example different acoustic alarms, will be generated. In this way it is possible to inform the patient that, for example, the weight load being borne is now in a critical range and should by no means be maintained, or that the continuation of a partial weight bearing load in this range for a relatively long period of time might be detrimental to the therapy.

Figure 2:
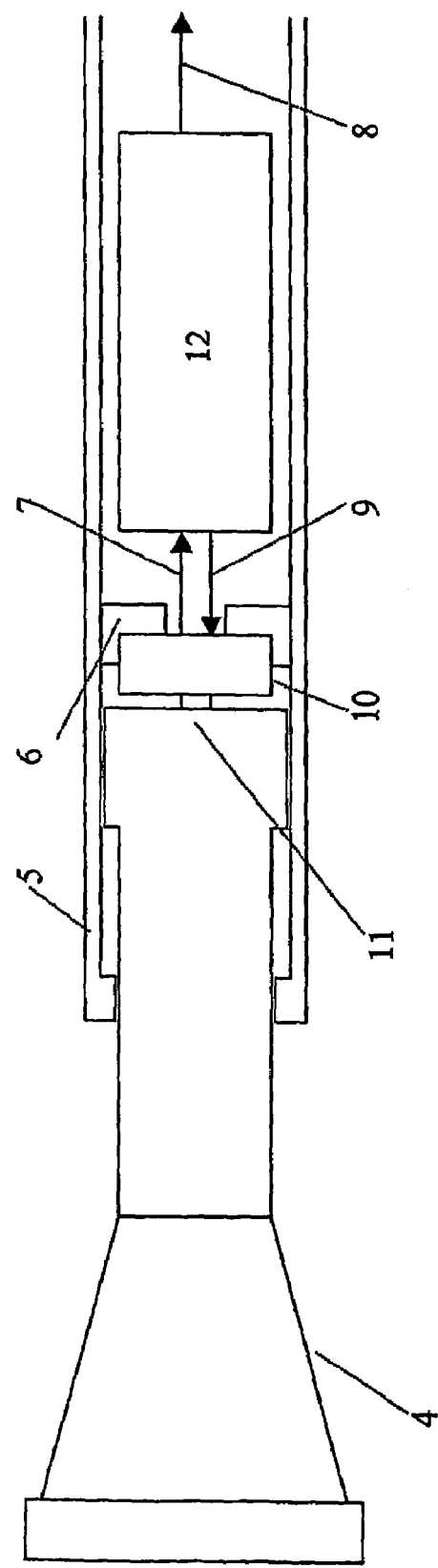
Figure 3:
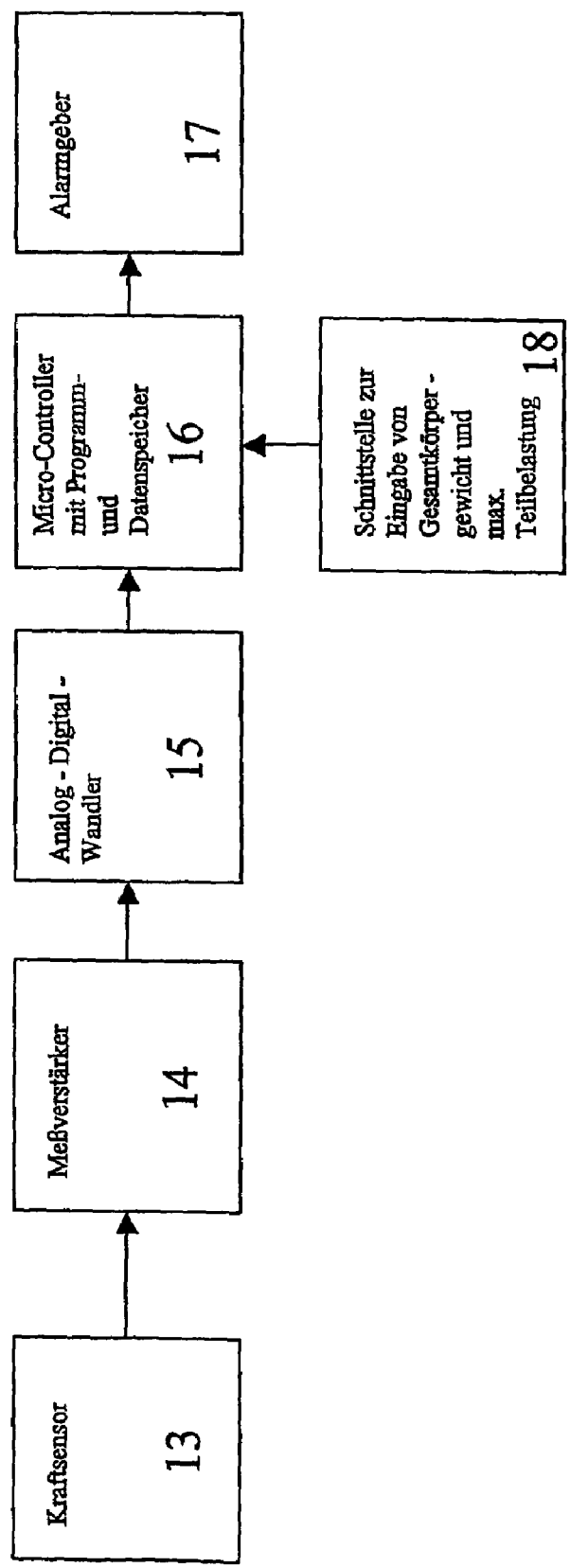

The invention is explained in greater detail below with reference to drawings, in which FIG. 1 is a graph demonstrating the weight bearing conditions prevailing when walking with crutches and practicing partial weight bearing under ideal static conditions, FIG. 2 shows an embodiment of a system of the invention, and FIG. 3 illustrates diagrammatically the layout of an appropriate electronic evaluation circuit.

The weight load on the partial weight bearing leg is determined as follows: during walking there is continuous alternation of standing leg phases and moving leg phases both for the healthy leg and for the leg requiring partial weight bearing therapy. In the standing leg phase of the partial weight bearing leg a weight loading 2+3 is exerted on this leg and on the two crutches together, this corresponding to the total body weight 1. When one leg changes from the moving phase to the standing phase and the other leg vice versa, there is a continuous change of load, which we will refer to as the transition phase B. FIG. 1 is a graph describing the weight bearing conditions when walking with crutches and practicing partial weight bearing under ideal circumstances.

Section A represents a standing leg phase of the healthy leg. The weight load on the healthy leg is equal to the entire body weight BW, since both the crutches and the injured leg are off the ground during this phase. The sections B show the alternation of the standing phase between the healthy leg and the injured leg and vice versa and section C illustrates the standing leg phase of the injured leg. Curve 1 represents the weight load on the injured leg when no crutches are used. Curve 2 shows the weight load on the crutches alone when crutches are used. At the beginning and end of the standing leg phase of the partial weight bearing leg the weight load on the injured leg always reaches a maximum due to the use of crutches, since in its standing leg phase the injured leg reaches the ground after a time delay and leaves the ground before the end of said phase—curve 3.

The actual partial weight loading is found by determining the height of the minimum value between the peaks of curve 2 produced in the course of the standing leg phase of the partial weight bearing leg. The total body weight less said minimum value gives the maximum weight load PL on the partial weight bearing leg during the course of its standing leg phase. It is equal to the peak of curve 3 in FIG. 1.

A brief overview of the symbols used in FIG. 1 is given below:
A: standing leg phase of the healthy leg
B: transition phase
C: standing leg phase of the partial weight bearing leg
BW: total body weight
PL: maximum partial weight load found
"1": total load on the partial weight bearing leg and crutches
"2": load on the crutches alone
"3": load on the partial weight bearing leg calculated as a differential curve from 1 and 2.

As shown in FIG. 2, the bottom portion (or any other suitable part) of each of the two crutches contains a power absorber 10 such as a load cell, a diaphragm-type sensor equipped with a strain gage, or a strain gage or the like mounted directly on the outside of the crutch, which power absorber will measure the actual weight load on the crutch. The power absorber will produce an analog signal, which is proportional to the weight load on the respective crutch, and is amplified and digitized by the circuit 12.

The measurements in one of the crutches are carried out at a constant measuring rate, and the resulting digitized signals are sent to the other crutch by radio transmission. This radio transmission could be effected by, say, a simple telemetry system based on ASK (Amplitude Shift Key Modulation) or FSC (Frequency Shift Key Modulation) at a transmission frequency in one of the ISM (Industry-Science-Medicine) frequency ranges, or alternatively a Bluetooth radio interface might be used.

The second crutch receives these data, after which a measurement is carried out in this crutch also. Thus the first crutch functions as 'master', since measurement of the weight loading is carried out herein fully independently, whilst the second crutch assumes the role of 'slave', since a measurement only takes place therein after an absolute measured value has been received from the first crutch. In the second crutch (slave) the two measured values are added together, and the resulting sum of the measured values of the two crutches corresponds to the total body weight less the weight load on the partial weight bearing leg, apart from dynamic influences resulting from shock movements and falling movements, as primarily occur at the beginning and end of a pace.

The sum of the two measured values is continuously processed in the crutch functioning as slave by a microcontroller 16 which calculates the actual partial weight load with the aid of an algorithm of the aforementioned type with or without dynamic enhancement. When the maximum permissible partial weight load is exceeded a signal tone 17 sounds. Instead of an acoustic signal generator, use may be made of a vibration motor, for example one built into the handle of one of the crutches.

This crutch may also contain a memory device that will store the partial weight load occurring at each pace or just the number of times the predefined partial weight bearing limit has been exceeded. In this case it would be possible to break the information down into, say, the number of times the partial weight bearing limit has been exceeded or the number of times this limit has been exceeded or fallen short of by, say, more than 5 kg or more than 10 kg, etc.

These stored data can afterwards be sent to a computer via a wireless or cable connection 18 (for example using a serial computer interface or USB), where it can be further processed. Another possibility is for the data to be transmitted in real time via radio (e.g., Bluetooth) to a computer, where it will be processed and stored externally. This could then be implemented, for example, by medical personelle when carrying out a walk analysis in real time in the therapeutic treatment room.

In an advantageous embodiment of the measuring device, a lower limit of the partial weight load can be set and when the load falls short of this limit again one of the aforementioned alarms will be generated, this being different from the alarm produced when a limit is exceeded. Likewise, a visible digital display (LED or LCD) could be built into the front part of the crutch handle, which would make it possible to provide a direct indication of the partial weight load occurring during the foregoing pace.

If the crutches are used in a therapeutically undesirable manner, such as running, this can be recognized by the electronic evaluation circuit 12, and, as a result, an alarm can again be given and the occurrence of this undesirable type of use stored in memory.

The body weight and the upper and lower partial weight bearing limits can be set with the aid of a computer or some other external apparatus, and the transmission of these settings can take place, for example, via a cable-jointing interface or radio transmission interface or infrared interface 18.

Another possibility is for one of the crutches to have a keypad and display mounted thereon, so that one or more of these settings can be made directly on the crutch.

Power is provided by, e.g., batteries installed in or on the crutch. Advantageously, these batteries can be rechargeable. They may be disposed in cavities in the crutch, if desired. A connector may be provided at the protected upper end of this part for connection of a battery charger. In order to keep the crutch in a usable state for as long as possible on one battery charge, it is advantageous to provide a stand-by mode which can be automatically assumed by the circuit when no load is placed on the crutch over a certain period of time, such as when the user is sitting or sleeping. The sensors and the entire electronics can be accommodated in the crutch tube, and the crutches will therefore have to be splash-proof. The sensors and electronics will have to be insensitive to temperature fluctuations and must be shock-proof.

Another way of determinating the partial weight load involves the direct measurement thereof by means of force sensors or pressure sensors accommodated in an insole or in a walking heel of a walking cast or directly in the sole of a shoe. The technical implementation would here be the same as in the method mentioned above but with the difference that in this case direct measurement of the weight load on the leg concerned is possible. The measuring parameters could be transmitted for analysis purposes via a wireless connection to data processing apparatus as mentioned above and present in at least one of the two crutches.

REFERENCE CHARACTERS

A: standing leg phase of the healthy leg
B: transition phase
C: standing leg phase of the partial weight bearing or injured leg
BW: body weight
PL: maximum partial weight load found
1 total load on the partial weight bearing leg and crutches
2 load on the crutches alone
3 load on the partial weight bearing leg as a differential curve calculated from 1 and 2
4 crutch foot of rubber
5 crutch tube
6 means for mounting the load cell
7 analog output signal
8 line to the signal generator
9 power supply for the load cell
10 load cell
11 plunger for transferring the weight load to the load cell
12 electronic evaluation circuit (FIG. 3)
13 force sensor
14 measuring amplifier
15 ADC (analog-to-digital converter)
16 microcontroller with a program for analyzing the digitized measurements
17 alarm signal generator
18 computer interface for inputting the body weight and partial weight bearing limit, and also for reading the partial weight overloads

The invention claimed is:

1. A system for measuring and monitoring the partial weight load borne by orthopedic and surgical patients, comprising at least one measuring device for direct or indirect determination of the weight load on at least one lower extremity, at least one alarm signal generator (17) adapted to give an alarm signal when the partial weight load exceeds an adjustable partial weight bearing limit, at least one evaluation unit, and also crutches, characterized in that the evaluation unit is built into a crutch and
   a) said at least one measuring device is built into the sole of a shoe or into an insole or into the walking heel of a walking cast, or
   b) said measuring devices are built into both crutches and the measurement of the partial weight load takes place in the first crutch (master) irrespective of measurements in the second crutch (slave), and a measurement is only carried out in said second crutch after a measured value attained in said first crutch has been transmitted to said second crutch.

2. A system as defined in claim 1, characterized in that said measuring devices are provided in shoe soles or insoles, and the measurement of the partial weight loading takes place in the first sole or insole (master) irrespective of measurements in the second sole or insole (slave) and measurement in said second sole or insole is only carried out after a measured value acquired in said first sole or insole has been transmitted to said second sole or insole.

3. A system as defined in claim 1, characterized in that said at least one evaluation unit and the alarm signal generator (17) are built into crutches.

4. A system as defined in claim 1, characterized in that the transmission of the measured values is effected by means of radio transmission.

5. A system as defined in claim 1, characterized in that the body weight less the sum of the measured values acquired in the two crutches corresponds to the weight load on the lower extremity, whilst it is optionally possible to determine the dynamic weight load through an algorithm.

6. A system as defined in claim 1, characterized in that said at least one alarm signal generator (17) is adapted to give an acoustic alarm when the partial weight loading exceeds or falls short of an adjustable weight load limit.

7. A system as defined in claim 1, characterized in that said at least one alarm signal generator (17) is adapted to give a vibration alarm when the partial weight load exceeds or falls short of an adjustable partial weight load limit.

8. A system as defined in claim 1, characterized in that when the partial weight loading has a value above or below an adjustable weight load limit these values are recorded and stored in an electronic non-volatile memory.

9. A system as defined claim 1, characterized in that a plurality of adjustable upper and lower limits is provided.

* * * * *

UNITED STATES PATENT AND TRADEMARK OFFICE
CERTIFICATE OF CORRECTION

PATENT NO. : 7,610,802 B2  Page 1 of 1
APPLICATION NO. : 10/559250
DATED : November 3, 2009
INVENTOR(S) : Clar et al.

It is certified that error appears in the above-identified patent and that said Letters Patent is hereby corrected as shown below:

On the Title Page:

Change from: "(86) PCT No.: PCT/AT03/00173"

To: --(86) PCT No.: PCT/AT03/000173--.

Signed and Sealed this

Fifteenth Day of June, 2010

David J. Kappos
*Director of the United States Patent and Trademark Office*